United States Patent
Terada

(10) Patent No.: US 7,838,478 B2
(45) Date of Patent: Nov. 23, 2010

(54) HAIR DETERGENT COMPOSITIONS

(75) Inventor: Eiji Terada, Tokyo (JP)

(73) Assignee: Kao Corporation, Tokyo (JP)

( * ) Notice: Subject to any disclaimer, the term of this patent is extended or adjusted under 35 U.S.C. 154(b) by 322 days.

(21) Appl. No.: 10/522,620

(22) PCT Filed: Aug. 8, 2003

(86) PCT No.: PCT/JP03/10139

§ 371 (c)(1),
(2), (4) Date: Jan. 31, 2005

(87) PCT Pub. No.: WO2004/014327

PCT Pub. Date: Feb. 19, 2004

(65) Prior Publication Data

US 2006/0166845 A1    Jul. 27, 2006

(30) Foreign Application Priority Data

Aug. 9, 2002  (JP)  ............. 2002-232733

(51) Int. Cl.
C11D 1/14   (2006.01)
C11D 1/29   (2006.01)
C11D 3/20   (2006.01)
C11D 3/37   (2006.01)

(52) U.S. Cl. ............. 510/122; 510/127; 510/130; 510/137; 510/466; 510/477; 510/488; 510/500; 510/501; 510/505; 510/506; 424/70.12; 424/70.24

(58) Field of Classification Search ............ 510/122, 510/127, 130, 137, 466, 477, 488, 500, 501, 510/505, 506; 424/70.12, 70.24
See application file for complete search history.

(56) References Cited

U.S. PATENT DOCUMENTS

| | | | |
|---|---|---|---|
| 4,185,087 A | 1/1980 | Morlino | |
| 4,409,267 A | 10/1983 | Ichinohe et al. | |
| 5,137,715 A * | 8/1992 | Hoshowski et al. | 424/70.17 |
| 5,302,322 A | 4/1994 | Birtwistle | |
| 5,627,148 A | 5/1997 | Dubief et al. | |
| 5,650,383 A | 7/1997 | Dubief et al. | |
| 5,807,956 A | 9/1998 | Czech | |
| 5,855,625 A * | 1/1999 | Maurer et al. | 8/137 |
| 6,153,570 A | 11/2000 | Decoster | |
| 6,171,515 B1 * | 1/2001 | Evans et al. | 252/8.81 |
| 6,262,007 B1 * | 7/2001 | Scialla et al. | 510/372 |
| 6,506,261 B1 * | 1/2003 | Man | 134/39 |
| 6,528,070 B1 * | 3/2003 | Bratescu et al. | 424/401 |
| 6,838,427 B2 * | 1/2005 | Ushio et al. | 510/515 |
| 2002/0077265 A1 * | 6/2002 | Buzzacarini et al. | 510/296 |

FOREIGN PATENT DOCUMENTS

| | | |
|---|---|---|
| EP | 0 181 773 B1 | 5/1986 |
| EP | 0 855 178 B1 | 7/1998 |
| EP | 0 978 272 A1 | 2/2000 |
| JP | 55-66506 | 5/1980 |
| JP | 57 058605 | 4/1982 |
| JP | 5-194154 | 8/1993 |
| JP | 8-301724 | 11/1996 |
| WO | 89 04180 | 5/1989 |
| WO | 03 066007 | 8/2003 |

OTHER PUBLICATIONS

Yasushi Watanabe, et al. "Hair Science", Japan Hair Science Association, Jan. 10, 1996, p. 31 (partial English translation attached).
"Dow Corning® 8500 Conditioning Agent", Dow Corning, Jan. 28, 2002, 3 pages.

* cited by examiner

*Primary Examiner*—Gregory R Del Cotto
(74) *Attorney, Agent, or Firm*—Oblon, Spivak, McClelland, Maier & Neustadt, L.L.P.

(57) ABSTRACT

Provided is a hair detergent composition comprising the following components (a), (b), and (c): (a) and anionic surfactant, (b) a carboxylic acid selected from hydroxymonocarboxylic acids, dicarboxylic acids, and hydroxydicarboxylic acids, or a salt thereof, and (c) silicone derivative having a group containing both a hydroxyl group and a nitrogen atom as a side chain thereof bonded to a silicon atom. The hair detergent composition provides rich foaming during shampooing and at the same time is capable of giving excellent conditioning effects and luster to the hair.

10 Claims, No Drawings

HAIR DETERGENT COMPOSITIONS

FIELD OF THE INVENTION

The present invention relates to silicone-containing hair detergent compositions which may provide benefits such as rich foaming during shampooing and excellent conditioning effects and luster to the hair.

BACKGROUND OF THE INVENTION

Although a water soluble cationized polymer has been used in hair detergents for the purpose of giving conditioning effects to the hair, it does not provide a satisfactory effect. Amino-modified silicones have been used as another material for giving excellent conditioning effects to the hair, but they did not exhibit their function sufficiently in hair detergents.

SUMMARY OF THE INVENTION

According to the present invention, there is thus provided a hair detergent composition comprising the following components (a), (b) and (c):
(a) an anionic surfactant,
(b) a carboxylic acid selected from the group consisting of hydroxymonocarboxylic acids, dicarboxylic acids and hydroxydicarboxylic acids, a salt thereof, and mixtures thereof and
(c) a silicone derivative having a group containing both a hydroxy group and a nitrogen atom as a side chain thereof bonded to a silicon atom.

DETAILED DESCRIPTION OF THE INVENTION

All publications cited herein are hereby incorporated by reference.

The present invention relates to a hair detergent composition providing good foaming during shampooing and which is capable of giving excellent conditioning effects and luster to the hair.

The present inventors have found that a hair detergent composition satisfying the above-described demand is obtainable by using, in combination, an anionic surfactant, a carboxylic acid, and a silicone derivative having a side chain containing both a hydroxy group and a nitrogen atom.

As the anionic surfactant of Component (a), sulfate-, sulfonate- and carboxylate-type surfactants are preferred. Specific examples include alkyl sulfates, polyoxyalkylene alkyl ether sulfates, polyoxyalkylene alkenyl ether sulfates, alkyl sulfosuccinates, polyoxyalkylene alkyl sulfosuccinates, polyoxyalkylene alkylphenyl ether sulfates, and higher fatty acid salts. Among these, polyoxyalkylene alkyl ether sulfates and alkyl sulfates are preferred, with those represented by the following formula (a1) or (a2) being particularly preferred.

  (a1)

  (a2)

wherein, R represents a $C_{10-18}$ alkyl or alkenyl group, R' represents a $C_{10-18}$ alkyl group, M represents an alkali metal, alkaline earth metal, ammonium, alkanolamine or basic amino acid, and n stands for a number of from 1 to 5 on weight average.

As Component (a), the above-described surfactants may be used as a combination of two or more thereof. The content of Component (a) in the hair detergent composition of the invention preferably ranges from 0.5 to 60 wt. %, more preferably from 1 to 30 wt. %, especially preferably from 8 to 20 wt. %, from the viewpoints of foaming performance, liquid state during use and detergency.

Examples of the hydroxymonocarboxylic acid serving as Component (b) include glycolic acid, lactic acid, hydroxyacrylic acid, oxybutyric acid and glyceric acid, among which lactic acid and glycolic acid are especially preferred. Examples of the dicarboxylic acid include malonic acid, succinic acid, glutaric acid, adipic acid, maleic acid, fumaric acid, phthalic acid and oxalic acid, among which maleic acid is especially preferred. Examples of the hydroxydicarboxylic acid include malic acid and tartaric acid, among which malic acid is especially preferred.

As Component (b), these compounds may be used either singly or in combination as a combination of two or more thereof. The content of Component (b) in the hair detergent composition of the invention ranges preferably from 0.05 to 10 wt. %, more preferably from 0.1 to 5 wt. %, especially preferably from 0.5 to 2 wt. % from the viewpoints of improvement in the finish of the hair such as luster and styling ease.

The silicone derivative as Component (c) has a group containing both a hydroxy group and a nitrogen atom as a side chain thereof bonded to a silicon atom. Preferred specific examples include those represented by the following average formula (1):

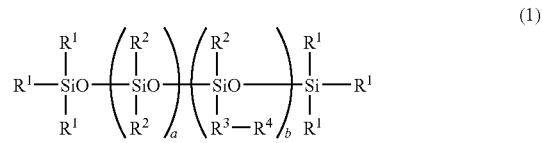

wherein, $R^1$ each independently represents a monovalent hydrocarbon group, a hydroxy group or an alkoxy group, $R^2$ each independently represents a monovalent hydrocarbon group, $R^3$ each independently represents a divalent $C_{1-10}$ hydrocarbon group, $R^4$ each independently represents a group represented by the following formula (2) or (3):

wherein, Y each independently represents a hydrogen atom or a group: —$CH_2CH(OH)$—$R^3$—OH ($R^3$ has the same meaning as described above), $R^5$ each independently represents a hydrogen atom or a group —$R^3NY_2$ (Y and $R^3$ have the same meanings as described above), with the proviso that all the Ys do not represent a hydrogen atom simultaneously, a stands for a number of from 25 to 1,000, b stands for a number of from 1 to 200.

Examples of the monovalent hydrocarbon group as $R^1$ include alkyl groups and aryl groups. As $R^1$, $C_{1-3}$ alkyl groups (particularly, methyl group) and $C_{1-15}$, especially $C_{10-15}$, alkoxy groups are preferred.

Examples of the monovalent hydrocarbon group as $R^2$ include $C_{1-6}$ alkyl groups such as methyl, ethyl, propyl, butyl, pentyl and hexyl, $C_{6-10}$ aryl groups such as phenyl, tolyl and xylyl, and $C_{6-10}$ aralkyl groups such as benzyl and phenethyl. Among these, an alkyl group, particularly a methyl group, is preferred.

Examples of the divalent $C_{1-10}$ hydrocarbon group as $R^3$ include methylene group, alkylene groups such as ethylene, trimethylene, propylene, tetramethylene, methyltrimethylene, ethylethylene and dimethylethylene groups, and alkylene-arylene groups such as a group represented by the formula: —$(CH_2)_2$—$C_6H_4$—. Among these, $C_{2-4}$ alkylene groups are preferred.

When Y represents a group: —$CH_2CH(OH)$—$R^3$—OH, it is preferably a 2,3-dihydroxypropyl group. As $R^4$, groups represented by the formula (3) are preferred, while as $R^5$, N-(2,3-dihydroxypropyl)aminoethyl and N,N-bis(2,3-dihydroxypropyl)aminoethyl groups are preferred.

It is preferred that a stands for a number of from 75 to 400 and b stands for a number of from 1 to 20.

The silicone derivative serving as Component (c) can be synthesized, for example, by reacting an amino-modified silicone with an epoxy functional compound such as glycidol as described in EP-0399706A2. Examples of the silicone derivative as Component (c) include compounds represented by the below-described formula, while those of commercially available products include "8500 Conditioning Agent" (CAS No. 237753-63-8; product of Dow Corning Corp).

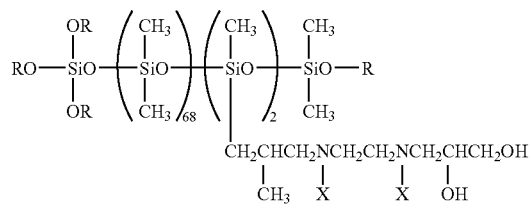

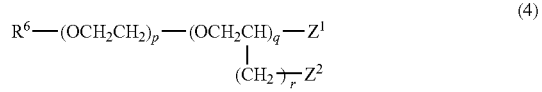

R: $C_{13}H_{27}$ to $C_{15}H_{31}$
X: 75% of —$CH_2CH(OH)CH_2OH$ and 25% of hydrogen atom As Component (c), two or more of the compounds as described above may be used in combination. From the viewpoints of smoothness and softness of the hair during the period of time from shampooing to rinsing, and smoothness of the hair after drying, the content of Component (c) in the hair detergent composition of the present invention preferably ranges from 0.05 to 4 wt. %, more preferably from 0.07 to 2 wt. %, especially preferably from 0.1 to 1.5 wt. %.

The hair detergent composition of the present invention may further contain, as Component (d), an organic solvent selected from the following (d1) to (d5):

(d1) compounds represented by formula (4):

$$R^6-(OCH_2CH_2)_p-(OCH_2CH)_q-Z^1$$
$$\quad\quad\quad\quad\quad\quad\quad\quad\quad\quad |$$
$$\quad\quad\quad\quad\quad\quad\quad\quad\quad\quad (CH_2)_r-Z^2$$

(4)

wherein, $R^6$ represents a hydrogen atom, a lower alkyl group or a group $R^7$-Ph-$R^8$— ($R^7$: a hydrogen atom, a methyl group or a methoxy group, $R^8$: a bond, or a saturated or unsaturated divalent $C_{1-3}$ hydrocarbon group, Ph: a paraphenylene group), $Z^1$ and $Z^2$ each represents a hydrogen atom or a hydroxy group, and p, q and r each stands for an integer of from 0 to 5, with the proviso that when p=q=0, $Z^1$ does not represent a hydrogen atom and $R^6$ represents neither a hydrogen atom nor a group $R^7$-Ph-, (d2) N-alkylpyrrolidones having a $C_{1-18}$ alkyl group bonded to the nitrogen atom, (d3) alkylene carbonates having 1 to 4 carbon atoms, (d4) polypropylene glycols having a molecular weight of from 200 to 5,000, and (d5) lactones or cyclic ketones represented by the following formulas (5), (6) or (7):

(5)

(6)

(7)

wherein, X represents a methylene group or an oxygen atom, $R^9$ and $R^{10}$ represent substituents, respectively, which are different from each other, and s and t each stands for a number of 0 or 1.

Among the organic solvents serving as Component (d), those corresponding to (d1) include ethanol, 1-propanol, 2-propanol, butanol, isobutanol, ethylene glycol, propylene glycol, 1,3-butanediol, benzyl alcohol, cinnamyl alcohol, phenethyl alcohol, p-anisyl alcohol, p-methylbenzyl alcohol, phenoxyethanol, 2-benzyloxyethanol, methylcarbitol, ethyl carbitol, propyl carbitol, butyl carbitol, triethylene glycol monoethyl ether, triethylene glycol monobutyl ether, and glycerin; those corresponding to (d2) include N-methylpyrrolidone, N-octylpyrrolidone and N-laurylpyrrolidone; those corresponding to (d3) include ethylene carbonate and propylene carbonate; and, as the propylene glycol of (d4), preferred is that having a molecular weight of from 200 to 1,000. In (d5), preferred examples of $R^9$ and $R^{10}$ in formulas (5) to (7) include linear, branched or cyclic alkyl groups, a hydroxy group, a sulfonic acid group, a phosphoric acid group, a carboxyl group, a phenyl group, sulfoalkyl groups, alkyl phosphate groups and carboxyalkyl groups. Among these, preferred are linear or branched $C_{1-6}$ alkyl groups, for example, methyl, ethyl, propyl, isopropyl and butyl groups, substituted at the γ-position in the case of γ-lactone and at the δ-position in the case of δ-lactone (the position of the methylene adjacent to the hetero oxygen atom). When enhancement of the water solubility of compounds (5) to (7) is desired, they preferably have, as $R^9$ or $R^{10}$, an acid group such as sulfonic acid group, phosphoric acid group or carboxy group, or an alkyl group substituted therewith. Examples of the lactone as (d5) include γ-butyrolactone, γ-caprolactone, γ-valerolactone, δ-valerolactone, δ-caprolactone and δ-heptanolactone. From the viewpoint of stability of the lactone, γ-lactones, especially γ-butyrolactone and γ-caprolactone are preferred. Examples of the cyclic ketone as (d5) include cyclopentanone, cyclohexanone, cycloheptanone and 4-methylcycloheptanone. As Component (d), particularly preferred are benzyl alcohol, benzyloxyethanol, propylene carbonate and propylene glycol.

As Component (d), two or more of the compounds as described above may be used in combination. The content of the Component (d) in the hair detergent composition of the invention preferably ranges from 0.01 to 50 wt. %, more preferably from 0.1 to 35 wt. %, especially preferably from 0.5 to 10 wt. %, from the viewpoints of improvement in feeling upon use, luster and flexibility.

To the hair detergent composition of the invention, a nonionic surfactant or amphoteric surfactant may be added in order to improve foaming performance.

Examples of the nonionic surfactant include polyoxyalkylene sorbitan fatty acid esters, polyoxyalkylene sorbit fatty acid esters, polyoxyalkylene glycerin fatty acid esters, polyoxyalkylene fatty acid esters, polyoxyalkylene alkyl ethers, polyoxyalkylene alkyl phenyl ethers, polyoxyalkylene (hydrogenated) castor oils, sucrose fatty acid esters, polyglycerin alkyl ethers, polyglycerin fatty acid esters, fatty acid alkanolamides and alkyl glycosides. Among these, alkyl glycosides, polyoxyalkylene alkyl ethers, polyoxyalkylene ($C_8$ to $C_{20}$) fatty acid esters, polyoxyethylene sorbitan fatty acid esters, polyoxyethylene hydrogenated castor oils, and fatty acid alkanolamides are preferred. As fatty acid alkanolamides, those having a $C_{8-18}$, especially $C_{10-16}$, acyl group are preferred. The fatty acid alkanolamides may be either monoalkanolamides or dialkanolamides, and those having a $C_{2-3}$ hydroxyalkyl group are preferred. Examples include oleic diethanolamide, palm kernel fatty acid diethanolamide, coconut fatty acid diethanolamide, lauric diethanolamide, polyoxyethylene coconut fatty acid monoethanolamide, coconut fatty acid monoethanolamide, lauric isopropanolamide and lauric monoethanolamide.

As the amphoteric surfactant, betaine surfactants are usable. Among these, alkyldimethylaminoacetic betaines and fatty acid amidopropyl betaines are more preferred, with fatty acid amidopropyl betaines being particularly preferred. The fatty acid amidopropyl betaines preferably have a $C_{8-18}$, especially $C_{10-16}$, acyl group. Among these, lauramidopropyl betaine, palm kernel amidopropyl betaine and cocamidopropyl betaine are especially preferred.

To the hair detergent composition of the present invention, a conditioning component selected from cationic polymers, cationic surfactants, silicones other than Component (c) and oils can be added in order to improve the finish after drying.

Examples of the cationic polymer include cationized cellulose derivatives, cationic starch, cationized guar gum derivatives, homopolymers of diallyl quaternary ammonium salts, diallyl quaternary ammonium salt/acrylamide copolymers, quaternized polyvinylpyrrolidone derivatives, polyglycol polyamine condensates, vinylimidazolium trichloride/vinylpyrrolidone copolymers, hydroxyethyl cellulose/dimethyldiallylammonium chloride copolymers, vinylpyrrolidone/quaternized dimethylaminoethyl methacrylate copolymers, polyvinylpyrrolidone/alkylamino acrylate copolymers, polyvinylpyrrolidone/alkylamino acrylate/vinylcaprolactam copolymers, vinylpyrrolidone/methacrylamidopropyl trimethylammonium chloride copolymers, alkylacrylamide/acrylate/alkylaminoalkylacrylamide/polyethylene glycol methacrylate copolymers, an adipic acid/dimethylaminohydroxypropyl ethylenetriamine copolymer ("Cartaretin", product of Sandoz/USA), and cationic polymers as described in Japanese Patent Laid-Open Nos. 139734/1978 and 36407/1985. Among these, cationized cellulose derivatives and cationized guar gum derivatives are particularly preferred.

Examples of the cationic surfactant include lauryl trimethyl ammonium chloride, cetyl trimethyl ammonium chloride, cetyl trimethyl ammonium bromide, stearyl trimethyl ammonium chloride, stearyl trimethyl ammonium bromide, lauryl trimethyl ammonium bromide, behenyl trimethyl ammonium chloride, dialkyl dimethyl ammonium chloride, dicetyl dimethyl ammonium chloride, distearyl dimethyl ammonium chloride, dicocoyl dimethyl ammonium chloride, myristyl dimethyl benzyl ammonium chloride, stearyl dimethyl benzyl ammonium chloride, lanolin fatty acid amidopropyl ethyldimethyl ammonium ethyl sulfate, lanolin fatty acid amidoethyl triethyl ammonium ethyl sulfate, stearyl amidopropyl dimethylamine (and salts thereof), stearyl amidoethyl diethylamine (and salts thereof), stearoxy propyl dimethylamine (and salts thereof), stearoxy propyl trimethyl ammonium chloride, lanolin fatty acid amidopropyl triethyl ammonium ethyl sulfate, lanolin fatty acid amidoethyl trimethyl ammonium methyl sulfate, lanolin fatty acid amidopropyl ethyldimethyl ammonium methyl sulfate, isoalkanoic acid ($C_{14-20}$) amidopropyl ethyldimethyl ammonium ethyl sulfate, isoalkanoic acid ($C_{18-22}$) amidopropyl ethyldimethyl ammonium ethyl sulfate, isostearic acid amidopropyl ethyldimethyl ammonium ethyl sulfate, isononanoic acid amidopropyl ethyldimethyl ammonium ethyl sulfate and alkyl trimethyl ammonium saccharine.

As the silicones other than Component (c), the following compounds can be given as examples.

(Silicones-1) Dimethylpolysiloxane

Examples include compounds represented by the 5 following formula:

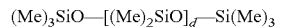

$(Me)_3SiO—[(Me)_2SiO]_d—Si(Me)_3$ wherein, Me represents a methyl group and d stands for a number of from 3 to 2,000.

(Sililcones-2) Amino-Modified Silicone

Various amino-modified silicones are usable, but those having an average molecular weight of from about 3,000 to 100,000 and described under the name of Amodimethicone in the CTFA Dictionary (Cosmetic Ingredient Dictionary, USA), third edition are particularly preferred. This amino-modified silicone is preferably employed in the form of an aqueous emulsion and "SM 8704C" (product of Dow Corning Toray Silicone), "DC 929" (product of Dow Corning), etc. are the commercially available products of the aqueous emulsion.

(Silicones-3) The Other Silicones

In addition to the above-described silicones, usable are polyether-modified silicones, methylphenyl polysiloxane, fatty acid-modified silicones, alcohol-modified silicones, alkoxy-modified silicones, epoxy-modified silicones, fluorine-modified silicones, cyclic silicones, and alkyl-modified silicones.

The term "oils" to be used herein as the conditioning component means an oily substance other than silicones and examples include hydrocarbons such as squalene, squalane, liquid paraffin, liquid isoparaffin and cycloparaffin; glycerides such as castor oil, cacao oil, mink oil, avocado oil and olive oil; waxes such as beeswax, spermaceti, lanolin and carnauba wax; alcohols such as cetyl alcohol, oleyl alcohol, stearyl alcohol, isostearyl alcohol, 2-octyldodecanol and glycerin; esters such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate; higher fatty acids such as capric acid, lauric acid, myristic acid, palmitic acid, stearic acid, behenic acid, oleic acid, coconut fatty acid, isostearic acid and isopalmitic acid; and isostearyl glyceryl ether and polyoxypropylene butyl ether. Among these, esters, particularly hexadecyl 2-ethylhexanoate, isononyl isononanoate and isopropyl palmitate, are particularly preferred.

As the conditioning component, two or more of these compounds may be used in combination. Its content in the hair detergent composition of the invention ranges preferably from 0.05 to 10 wt. %, more preferably from 0.07 to 5 wt. %, especially preferably from 0.1 to 2 wt. % from the viewpoints of lubrication of foams, and smoothness during the period of time from shampooing to rinsing.

In addition to the above-described components, components conventionally used for a hair detergent can be incorporated in the hair detergent composition of the present invention, depending on the purpose. Such optional components include antidandruff, vitamins, bactericides, anti-inflammatory agents, antiseptics, chelating agents, humectants such as sorbitol and pantenol, colorants such as dyes and pigments, viscosity regulators such as hydroxyethyl cellulose, methyl cellulose, polyethylene glycol and clay minerals; pH regulators such as potassium hydroxide; vegetable extracts; pearling agents; perfumes; coloring matters; ultraviolet absorbers; antioxidants; and the other components as described in the ENCYCLOPEDIA OF SHAMPOO INGREDIENTS (MICELLE PRESS).

The hair detergent compositions of the present invention are preferably adjusted to a pH (when diluted to 20 times the weight with water, at 25° C.) of 4.5 or less upon application to the hair from the viewpoint of imparting the hair with luster and flexibility. In order to prevent the compositions from causing irritation, their pH is preferably adjusted from 1 to 4.5, more preferably from 2 to 4.5, especially preferably from 3 to 3.9. For the adjustment of the pH, the carboxylic acid serving as Component (b) and also an alkali agent such as potassium hydroxide are usable.

Although the form of the hair detergent compositions of the invention can be selected as needed from liquid, powder, gel and granule, a liquid type using water as a solvent is preferred.

The hair detergent compositions of the invention are preferably used as a hair shampoo composition.

EXAMPLES

The following examples further describe and demonstrate embodiments of the present invention. The examples are given solely for the purpose of illustration and are not to be construed as limitations of the present invention.

Examples 1 to 3 and Comparative Examples 1 to 3

Shampoo compositions as shown in Table 1 were prepared and were organoleptically evaluated.

(Hair Washing Method)

After the hair was moistened sufficiently, 5 g or 10 g (5 g for medium-length hair and 10 g for long hair) of the shampoo composition was applied to the hair and the hair was washed therewith. The hair was then rinsed well with water, followed by sufficient drying with hot air from a dryer.

(Organoleptic Evaluation)

The shampoo compositions were evaluated by a panel of 10 experts based on the criteria described below and ranked based on the average score.

Evaluation Criteria (1) Softness of the Hair During Foaming
    4: Very soft
    3: Soft
    2: Slightly soft
    1: Slightly rigid
    0: Rigid (2) Smoothness of the Hair During Rinsing and After Drying
    4: Very smooth
    3: Smooth
    2: Slightly smooth
    1: Not so smooth
    0: Not smooth (3) Luster of the Hair After Drying
    4: A marked improvement in luster is observed.
    3: An improvement in luster is observed.
    2: A slight improvement in luster is observed.
    1: No improvement in luster is observed.
    0: Luster is lost.

Rank
    A: an average score of not less than 3.5
    B: an average score of not less than 2.5 but less than 3.5
    C: an average score of not less than 1.5 but less than 2.5
    D: an average score less than 1.5

TABLE 1

| | Composition (wt. %) | Examples | | | Comparative Examples | | |
|---|---|---|---|---|---|---|---|
| | | 1 | 2 | 3 | 1 | 2 | 3 |
| (a) | Sodium polyoxyethylene (2) lauryl ether sulfate | 10.0 | 10.0 | 10.0 | 10.0 | 10.0 | 10.0 |
| (b) | Malic acid | 1.0 | 1.0 | — | 1.0 | 1.0 | 1.0 |
| | Maleic acid | — | — | 1.0 | — | — | — |
| (c) | Silicone derivative* | 0.5 | 0.5 | 0.5 | 0.5 | — | — |
| Others | Propylene carbonate | 1.0 | — | 1.0 | 1.0 | 1.0 | 1.0 |
| | Benzyloxyethanol | — | 1.0 | — | — | — | — |
| | Amino-modified silicone ("KT1989", product of GE Toshiba Silicone) | — | — | — | — | — | 0.5 |
| | Cocamidopropyl betaine | 3.0 | 3.0 | 3.0 | 3.0 | 3.0 | 3.0 |
| | Cocamide MEA | 1.0 | 1.0 | 1.0 | 1.0 | 1.0 | 1.0 |
| | Ethylene glycol distearyl ester | 1.0 | 1.0 | 1.0 | 1.0 | 1.0 | 1.0 |
| | Cationized cellulose ("UCare Polymer JR-400", product of Amerchol) | 0.5 | 0.5 | 0.5 | 0.5 | 0.5 | 0.5 |

TABLE 1-continued

| Composition (wt. %) | | Examples | | | Comparative Examples | | |
|---|---|---|---|---|---|---|---|
| | | 1 | 2 | 3 | 1 | 2 | 3 |
| | Sodium chloride | 0.5 | 0.5 | 0.5 | 0.5 | 0.5 | 0.5 |
| | Perfume | Trace | Trace | Trace | Trace | Trace | Trace |
| | Aqueous solution of sodium hydroxide | q.s. | q.s. | q.s. | q.s. | q.s. | q.s. |
| | Purified water | Balance | Balance | Balance | Balance | Balance | Balance |
| | pH (after diluted to 20 times the weight) | 3.5 | 3.5 | 3.5 | 6.0 | 3.5 | 3.5 |
| Evaluation | Softness of hair during foaming | A | A | A | A | C | B |
| | Smoothness of hair during rinsing | A | A | A | A | C | D |
| | Smoothness of hair after drying | A | A | A | B | C | C |
| | Luster upon drying | A | A | A | C | B | C |

*silicone derivative:

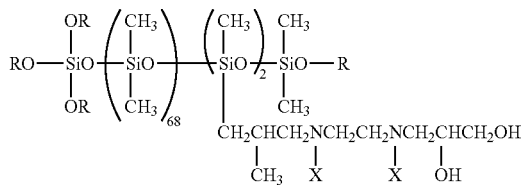

R: $C_{13}H_{27}$ to $C_{15}H_{31}$
X: 75% of —$CH_2CH(OH)CH_2OH$ and 25% of hydrogen atom

Example 4

Conditioning Shampoo

| | (wt. %) |
|---|---|
| Sodium polyoxyethylene (2) lauryl ether sulfate | 11.0 |
| Lactic acid | 0.75 |
| Malic acid | 0.25 |
| Silicone derivative *1 | 1.0 |
| Polypropylene glycol ($M_w$ = 400) | 0.5 |
| Cocamidopropyl betaine | 3.0 |
| Cocamide MEA | 0.5 |
| Ethylene glycol distearyl ester | 1.0 |
| Cationized guar gum ("Jaguar C-13S", product of RHODIA) | 0.4 |
| Sodium chloride | 0.3 |
| Perfume | trace |
| Aqueous solution of sodium hydroxide | q.s. |
| Purified water | Balance |

*1 sold from Dow Corning under the name of "8500 CONDITIONING AGENT". It contains, as an effective ingredient, 60 wt. % of a silicone derivative (CAS No. 237753-63-8) having a group containing both a hydroxy group and a nitrogen atom as a side chain.

It has been found that the shampoo (having pH 3.9 when diluted to 20 times the weight) thus obtained was excellent in smoothness during the period of time from foaming to rinsing, smoothness after drying and luster.

Example 5

Conditioning Shampoo

| | (wt. %) |
|---|---|
| Sodium polyoxyethylene (2) lauryl ether sulfate | 10.0 |
| Sodium lauryl sulfate | 5.0 |
| Malic acid | 0.5 |
| Lactic acid | 0.5 |
| Silicone derivative *1 | 0.3 |
| Benzyl alcohol | 0.5 |
| N-methylpyrrolidone | 0.2 |
| Cyclohexanone | 0.2 |
| Cocamide MEA | 1.0 |
| Myristyl alcohol | 1.0 |
| Cetanol | 0.5 |
| Behenyl trimonium chloride | 0.3 |
| Dimethyl polysiloxane (viscosity: 100,000 mPa · s) | 0.3 |
| Glycerin | 1.0 |
| Ethylene glycol distearyl ester | 1.5 |
| Cationized guar gum ("Jaguar C-13S", product of RHODIA) | 0.4 |
| Sodium chloride | 0.2 |
| Perfume | trace |
| Aqueous solution of sodium hydroxide | q.s. |
| purified water | Balance |

*1 sold from Dow Corning under the name of "8500 CONDITIONING AGENT". It contains, as an effective ingredient, 60 wt. % of a silicone derivative (CAS No. 237753-63-8) having a group containing both a hydroxy group and a nitrogen atom as a side chain.

It has been found that the shampoo thus obtained (having pH of 3.7 when diluted to 20 times the weight) was excellent in smoothness during the period of time from foaming to rinsing, smoothness after drying and luster.

The invention claimed is:

1. A hair detergent composition, which has a pH at 25° C. of 4.5 or less when diluted to 20 times the weight with water, comprising the following components (a), (b), (c) and (d):

(a) at least one anionic surfactant in an amount of 0.5 to 60 wt %, wherein the anionic surfactant is represented by the following formula (a1) or (a2):

$$RO(CH_2CH_2O)_nSO_3M \quad (a1)$$

$$R'OSO_3M \quad (a2)$$

wherein R represents a $C_{10-18}$ alkyl or alkenyl group, R' represents a $C_{10-18}$ alkyl group, M represents an alkali metal, alkaline earth metal, ammonium, alkanolamine or basic amino acid, and n stands for a number of from 1 to 5 on weight average, (b) at least one carboxylic acid in an amount of 0.05 to 10 wt %, and selected from the group consisting of lactic acid, maleic acid and malic acid, (c) a silicone derivative in an amount of 0.05 to 4 wt %, which is Bis (C13-C15 Alkoxy) PG Amodimethicone, and (d) at least one organic solvent in an amount from 0.5 to 10 wt % selected from the group consisting of benzyloxyethanol and propylene carbonate, and wherein said composition excludes benzyl alcohol.

2. The hair detergent composition of claim 1, wherein Component (a) is present in an amount of 8 to 20 wt %, Component (b) is present in an amount of 0.5 to 2 wt %, and Component (c) is present in an amount of 0.1 to 1.5 wt %.

3. The hair detergent composition of claim 1, wherein said pH is from 3 to 3.9.

4. The hair detergent composition of claim 1, further comprising at least one conditioning component, which comprises at least one of cationic polymers, cationic surfactants, silicones other than component (c), and oils.

5. The hair detergent composition of claim 4, wherein the conditioning component is present in an amount of 0.05 to 10 wt %.

6. The hair detergent composition of claim 4, wherein the conditioning component is present in an amount of 0.1 to 2 wt %.

7. A method comprising washing hair with the hair detergent compositioon of claim 1.

8. The hair detergent composition of claim 1, wherein organic solvent (d) comprises benzyloxyethanol.

9. The hair detergent composition of claim 1, wherein Component (a) is at least one selected from the group consisting of sodium polyoxyethylene (2) lauryl ether sulfate and sodium lauryl sulfate.

10. The hair detergent composition of claim 1, wherein Component (d) comprises propylene carbonate.

* * * * *